(12) United States Patent
Braun

(10) Patent No.: US 7,982,612 B2
(45) Date of Patent: Jul. 19, 2011

(54) METHODS, APPARATUSES, AND COMPUTER PROGRAM PRODUCTS FOR MONITORING A VOLUME OF FLUID IN A FLEXIBLE FLUID BAG

(75) Inventor: Patrick Joseph Braun, Pittsburgh, PA (US)

(73) Assignee: McKesson Automation Inc., Cranberry, PA (US)

( * ) Notice: Subject to any disclaimer, the term of this patent is extended or adjusted under 35 U.S.C. 154(b) by 315 days.

(21) Appl. No.: 12/389,842

(22) Filed: Feb. 20, 2009

(65) Prior Publication Data

US 2010/0214106 A1 Aug. 26, 2010

(51) Int. Cl.
G08B 13/14 (2006.01)
G08B 21/00 (2006.01)

(52) U.S. Cl. .................. 340/572.1; 340/612; 340/618

(58) Field of Classification Search ............ 340/572.1, 340/539.12, 572.8, 573.1, 573.5, 603, 612, 340/613, 618, 686.1, 686.6; 128/903, 904; 600/300, 301
See application file for complete search history.

(56) References Cited

U.S. PATENT DOCUMENTS

| | | | |
|---|---|---|---|
| 4,717,042 A | 1/1988 | McLaughlin | |
| 4,785,969 A | 11/1988 | McLaughlin | |
| 4,847,764 A | 7/1989 | Halvorson | |
| 5,003,296 A * | 3/1991 | Lee | 340/618 |
| 5,014,875 A | 5/1991 | McLaughlin et al. | |
| 5,190,185 A | 3/1993 | Blechl | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A | 1/1997 | McDonald et al. | |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,797,515 A | 8/1998 | Liff et al. | |
| 5,805,456 A | 9/1998 | Higham et al. | |
| 5,842,976 A | 12/1998 | Williamson | |
| 5,878,885 A | 3/1999 | Wangu et al. | |
| 5,880,443 A | 3/1999 | McDonald et al. | |
| 5,883,806 A | 3/1999 | Meador et al. | |

(Continued)

*Primary Examiner* — John A Tweel, Jr.
(74) *Attorney, Agent, or Firm* — Alston & Bird LLP

(57) ABSTRACT

A method, apparatus, and computer program product are provided for monitoring a volume of fluid in a flexible fluid bag. A flexible fluid bag according to the invention may include a first and second side wall opposing each other, an outlet through which fluid contained in the fluid bag is evacuated, a signaling tag carried by the first side wall, and an inducer carried by the second side wall. The signaling tag and inducer may be positioned such that when a volume of fluid in the fluid bag is less than a predefined threshold, the signaling tag and inducer come into sufficient proximity due to flexation of at least a portion of the sidewalls of the fluid bag as fluid is evacuated from the fluid bag to trigger a state of a signal emitted by the signaling tag to change.

22 Claims, 5 Drawing Sheets

U.S. PATENT DOCUMENTS

| | | | |
|---|---|---|---|
| 5,893,697 A | 4/1999 | Zini et al. | |
| 5,905,653 A | 5/1999 | Higham et al. | |
| 5,912,818 A | 6/1999 | McGrady et al. | |
| 5,927,540 A | 7/1999 | Godlewski | |
| 5,940,306 A | 8/1999 | Gardner et al. | |
| 5,971,593 A | 10/1999 | McGrady | |
| 6,003,006 A | 12/1999 | Colella et al. | |
| 6,011,999 A | 1/2000 | Holmes | |
| 6,021,392 A | 2/2000 | Lester et al. | |
| 6,039,467 A | 3/2000 | Holmes | |
| 6,065,819 A | 5/2000 | Holmes et al. | |
| 6,068,156 A | 5/2000 | Liff et al. | |
| 6,109,774 A | 8/2000 | Holmes et al. | |
| 6,112,502 A | 9/2000 | Frederick et al. | |
| 6,116,461 A | 9/2000 | Broadfield et al. | |
| 6,151,536 A | 11/2000 | Arnold et al. | |
| 6,170,230 B1 | 1/2001 | Chudy et al. | |
| 6,176,392 B1 | 1/2001 | William et al. | |
| 6,189,727 B1 | 2/2001 | Shoenfeld | |
| 6,223,934 B1 | 5/2001 | Shoenfeld | |
| 6,256,967 B1 | 7/2001 | Hebron et al. | |
| 6,283,322 B1 | 9/2001 | Liff et al. | |
| 6,285,285 B1 * | 9/2001 | Mongrenier | 340/572.8 |
| 6,289,656 B1 | 9/2001 | Wangu et al. | |
| 6,337,631 B1 * | 1/2002 | Pai et al. | 340/618 |
| 6,338,007 B1 | 1/2002 | Broadfield et al. | |
| 6,339,732 B1 | 1/2002 | Phoon et al. | |
| 6,361,263 B1 | 3/2002 | Dewey et al. | |
| 6,370,841 B1 | 4/2002 | Chudy et al. | |
| 6,449,927 B2 | 9/2002 | Hebron et al. | |
| 6,471,089 B2 | 10/2002 | Liff et al. | |
| 6,497,342 B2 | 12/2002 | Zhang et al. | |
| 6,499,270 B2 | 12/2002 | Peroni et al. | |
| 6,532,399 B2 | 3/2003 | Mase | |
| 6,564,121 B1 | 5/2003 | Wallace et al. | |
| 6,581,798 B2 | 6/2003 | Liff et al. | |
| 6,609,047 B1 | 8/2003 | Lipps | |
| 6,611,733 B1 | 8/2003 | De La Huerga | |
| 6,625,952 B1 | 9/2003 | Chudy et al. | |
| 6,640,159 B2 | 10/2003 | Holmes et al. | |
| 6,650,964 B2 | 11/2003 | Spano, Jr. et al. | |
| 6,671,579 B2 | 12/2003 | Spano, Jr. et al. | |
| 6,681,149 B2 | 1/2004 | William et al. | |
| 6,690,280 B2 * | 2/2004 | Citrenbaum et al. | 340/612 |
| 6,742,671 B2 | 6/2004 | Hebron et al. | |
| 6,755,931 B2 | 6/2004 | Vollm et al. | |
| 6,760,643 B2 | 7/2004 | Lipps | |
| 6,776,304 B2 | 8/2004 | Liff et al. | |
| 6,785,589 B2 | 8/2004 | Eggenberger et al. | |
| 6,790,198 B1 | 9/2004 | White et al. | |
| 6,814,254 B2 | 11/2004 | Liff et al. | |
| 6,814,255 B2 | 11/2004 | Liff et al. | |
| 6,847,861 B2 | 1/2005 | Lunak et al. | |
| 6,874,684 B1 | 4/2005 | Denenberg et al. | |
| 6,892,780 B2 | 5/2005 | Vollm et al. | |
| 6,895,304 B2 | 5/2005 | Spano, Jr. et al. | |
| 6,975,922 B2 | 12/2005 | Duncan et al. | |
| 6,985,797 B2 | 1/2006 | Spano, Jr. et al. | |
| 6,996,455 B2 | 2/2006 | Eggenberger et al. | |
| 7,010,389 B2 | 3/2006 | Lunak et al. | |
| 7,014,063 B2 | 3/2006 | Shows et al. | |
| 7,016,766 B2 | 3/2006 | William et al. | |
| 7,040,504 B2 | 5/2006 | Broadfield et al. | |
| 7,052,097 B2 | 5/2006 | Meek, Jr. et al. | |
| 7,072,737 B2 | 7/2006 | Lunak et al. | |
| 7,072,855 B1 | 7/2006 | Godlewski et al. | |
| 7,077,286 B2 | 7/2006 | Shows et al. | |
| 7,085,621 B2 | 8/2006 | Spano, Jr. et al. | |
| 7,092,796 B2 | 8/2006 | Vanderveen | |
| 7,093,755 B2 | 8/2006 | Jordan et al. | |
| 7,100,792 B2 | 9/2006 | Hunter et al. | |
| 7,103,419 B2 | 9/2006 | Engleson et al. | |
| 7,111,780 B2 | 9/2006 | Broussard et al. | |
| 7,139,639 B2 | 11/2006 | Broussard et al. | |
| 7,150,724 B2 | 12/2006 | Morris et al. | |
| 7,171,277 B2 | 1/2007 | Engleson et al. | |
| 7,218,231 B2 | 5/2007 | Higham | |
| 7,228,198 B2 | 6/2007 | Vollm et al. | |
| 7,249,688 B2 | 7/2007 | Hunter et al. | |
| 7,348,884 B2 | 3/2008 | Higham | |
| 7,417,729 B2 | 8/2008 | Greenwald | |
| 7,419,133 B2 | 9/2008 | Clarke et al. | |
| 7,426,425 B2 | 9/2008 | Meek, Jr. et al. | |
| 7,554,449 B2 | 6/2009 | Higham | |
| 7,571,024 B2 | 8/2009 | Duncan et al. | |
| 7,588,167 B2 | 9/2009 | Hunter et al. | |
| 2008/0051937 A1 | 2/2008 | Khan et al. | |
| 2008/0195246 A1 | 8/2008 | Tribble et al. | |
| 2008/0195416 A1 | 8/2008 | Tribble et al. | |

* cited by examiner

METHODS, APPARATUSES, AND COMPUTER PROGRAM PRODUCTS FOR MONITORING A VOLUME OF FLUID IN A FLEXIBLE FLUID BAG

TECHNOLOGICAL FIELD

Embodiments of the present invention relate generally to medical technology and, more particularly, relate to methods, apparatuses, and computer program products for monitoring a volume of fluid in a flexible fluid bag, such as an intravenous (IV) bag.

BACKGROUND

IV bags are often used in medical environments for administration of liquid medication or other fluids to patients. As the fluid is evacuated from an IV bag and administered to a patient, the volume of fluid remaining in the bag decreases. Depending on the patient's medication regime, the IV bag may need to be replaced as the fluid in the IV bag runs out so that administration of fluid to the patient continues uninterrupted. Accordingly, medical personnel responsible for tending to the patient may need to be aware of a volume of fluid remaining in the IV bag so that the IV bag can be replaced when necessary.

Currently, however, nursing and pharmacy staffs often do not know the status of the fluid level within an IV bag that is connected to a patient and administering fluids. Since patients are often moved from department to department and their IV schedules interrupted, trying to determine volumes based on flow rates and start time of administration are not accurate. Since current methods do not offer sufficient accuracy, hospital pharmacies are often forced to overstock IV medications at the floor level to make sure the medication or other fluid is available when needed.

At some medical facilities, medical personnel perform IV rounds to note where IV bags are in their administration cycles to facilitate planning when the pharmacy should send new IV bags to the nurses attending the respective patients. This manual review of IV bag status may increase time and monetary costs of administering IVs as well as tracking issues. Nursing may replace an IV bag before it is empty because of lack of resources to recheck a volume of fluid remaining in the IV bag if the fluid in the IV bag were allowed to more fully empty. This situation may result in IV fluid being wasted through discarding a large number of IV bags with fluid remaining. In some circumstances, medical staff may arrive to check an IV bag status and/or replace an IV bag well after the IV bag has emptied. This situation may affect patients by interrupting administration of medication to the patient. Further, medical staff arriving after the IV bag has emptied may create a time management issue for medical staff because after discovery of the empty IV bag, medical personnel must retrieve a full IV bag from storage and go through the process of connecting the new IV bag for administration to the patient.

Accordingly, it would be advantageous to provide methods, apparatuses, and computer program products for more efficiently monitoring a volume of fluid in a flexible fluid bag.

BRIEF SUMMARY OF SOME EXAMPLES OF THE INVENTION

A method, apparatus, and computer program product are therefore provided for monitoring a volume of fluid in a flexible fluid bag. In this regard, embodiments of the invention provide a flexible fluid bag, such as may be used for administration of intravenous fluids, which facilitates detection when a volume of fluid remaining in the fluid bag is less than a predefined threshold. Embodiments of the invention further provide a method and computer program product for monitoring a volume of fluid in such flexible fluid bags to detect when the volume of fluid therein is less than the predefined threshold. Accordingly, embodiments of the invention enable detection of a low fluid volume level within a fluid bag and notification of the low fluid volume status when such a condition is detected.

In a first exemplary embodiment, a flexible fluid bag is provided. The fluid bag may be formed of pliable material and may comprise a first side wall. The fluid bag may further comprise a second side wall opposing the first side wall. The fluid bag may additionally comprise an outlet through which fluid contained in the fluid bag is evacuated. The fluid bag may also comprise a signaling tag carried by the first side wall and an inducer carried by the second side wall. The signaling tag and inducer may be positioned such that when a volume of fluid in the fluid bag is less than a predefined threshold, the signaling tag and inducer come into a sufficient proximity due to a flexation of at least a portion of one or more of the first or second sidewalls of the fluid bag as fluid is evacuated from the fluid bag to trigger a state of a signal emitted by the signaling tag to change.

In another exemplary embodiment, a method for monitoring a volume of fluid in a flexible fluid bag is provided. The method may include administering the fluid from the fluid bag to a recipient. The fluid bag may comprise a first side wall, a second side wall opposing the first side wall, an outlet through which fluid contained in the fluid bag is evacuated for administration to a recipient, a signaling tag carried by the first side wall, and an inducer carried by the second side wall. The method may further include detecting a change in state of a signal emitted by the signaling tag. The change in state of the signal may result from the signaling tag and inducer coming into a sufficient proximity of one another due to flexation of at least a portion of one or more of the first or second sidewalls of the fluid bag as fluid is evacuated therefrom. The change in state of the signal may be indicative of the volume of fluid in the fluid bag being below a predefined threshold.

In another exemplary embodiment, a computer program product is provided. The computer program product is for monitoring a volume of fluid in a flexible fluid bag. The fluid bag may comprise a first side wall, a second side wall opposing the first side wall, an outlet through which fluid contained in the fluid bag is evacuated for administration to a recipient, a signaling tag carried by the first side wall, and an inducer carried by the second side wall. The computer program product includes at least one computer-readable storage medium having computer-readable program instructions stored therein. The computer-readable program instructions may include a plurality of program instructions. Although in this summary, the program instructions are ordered, it will be appreciated that this summary is provided merely for purposes of example and the ordering is merely to facilitate summarizing the computer program product. The example ordering in no way limits the implementation of the associated computer program instructions. The first program instruction is for monitoring a state of a signal emitted by the signaling tag while fluid from the fluid bag is administered to a recipient. The second program instruction is for detecting a change in state of a signal emitted by the signaling tag as a result of the signaling tag and inducer coming into a sufficient proximity of one another due to flexation of at least a portion of one or more of the first or second sidewalls of the fluid bag as fluid is evacuated therefrom. The change in state of the signal may be indicative of the volume of fluid in the fluid bag being below a predefined threshold.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the invention in any way. It will be appreciated that the scope of the invention encompasses many potential embodiments, some of which will be further described below, in addition to those here summarized.

BRIEF DESCRIPTION OF THE DRAWING(S)

Having thus described embodiments of the invention in general terms, reference will now be made to the accompanying drawings, which are not necessarily drawn to scale, and wherein:

DETAILED DESCRIPTION

Figure 1:
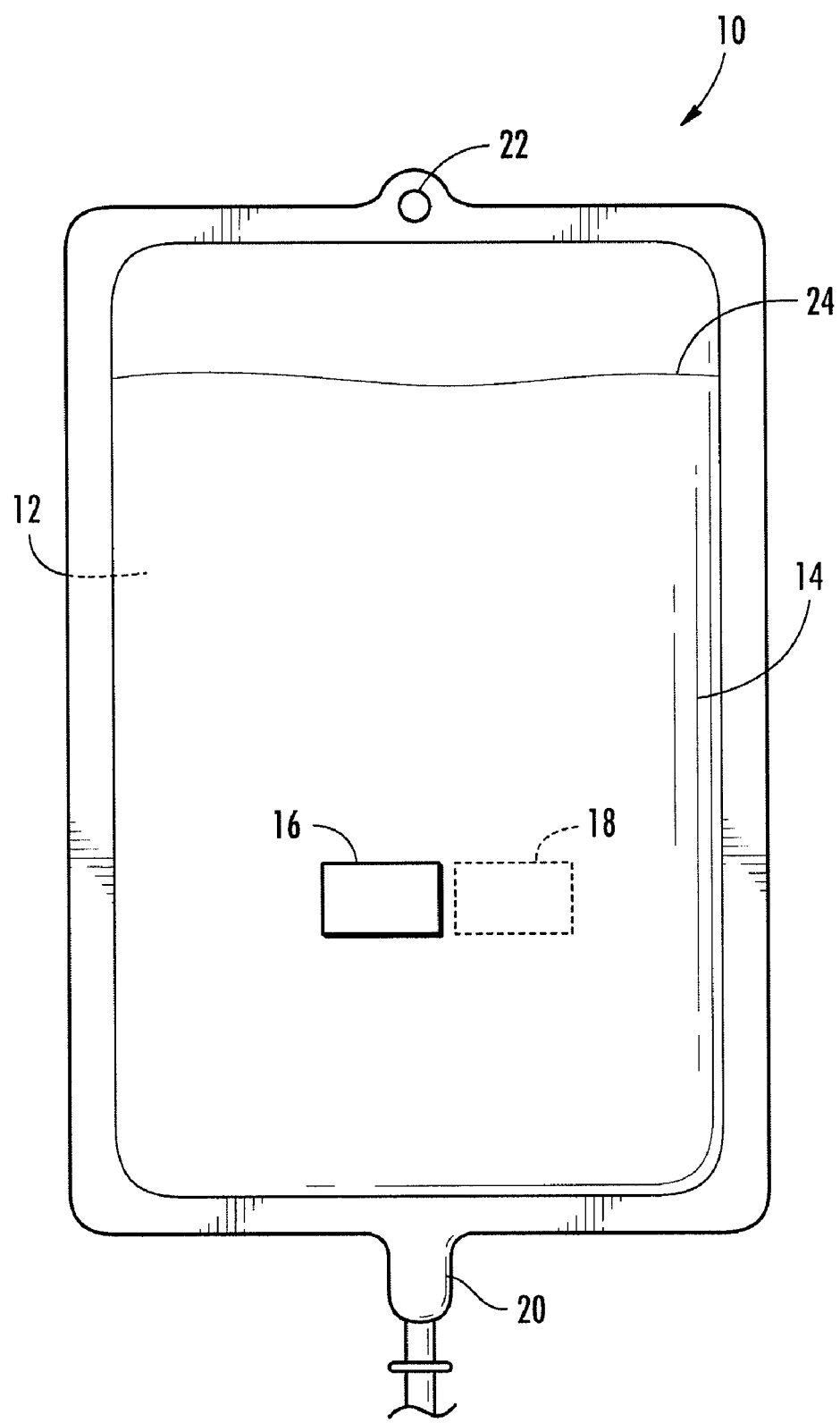
FIG. 1 illustrates a facing view of a flexible fluid bag according to an exemplary embodiment of the present invention.

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like reference numerals refer to like elements throughout.

FIG. 1 illustrates a facing view of a flexible fluid bag 10 according to an exemplary embodiment of the present invention. As used herein, "exemplary" merely means an example and as such represents one example embodiment for the invention and should not be construed to narrow the scope or spirit of the invention in any way. It will be appreciated that the scope of the invention encompasses many potential embodiments in addition to those illustrated and described herein for purposes of example. As such, while FIG. 1 illustrates one example of a configuration of a flexible fluid bag, numerous other configurations may also be used to implement embodiments of the present invention.

In some embodiments, the fluid bag 10 comprises an IV bag and the fluid contained therein may comprise a medication or other fluid that may be administered to a patient for medicinal purposes. The fluid bag 10 comprises a first side wall 12 and a second side wall 14 opposing the first side wall 12. The fluid bag 10 may be formed of any pliable material enabling flexation of at least a portion of the first side wall 10 or the second side wall 14 depending on the volume of fluid contained in the fluid bag. In this regard, the sidewalls of the fluid bag 10 may bulge or otherwise flex outward to accommodate larger volumes of fluid in the fluid bag 10 until the volume of the fluid reaches a full capacity level of the fluid bag 10. Similarly, the sidewalls of the fluid bag 10 may collapse or otherwise flex inward as fluid is evacuated from the fluid bag 10 through the outlet 20.

Fluid may be evacuated from the fluid bag 10 through any variety of means known in the art. For example, the fluid bag 10 may be hung from an IV pole or other apparatus and fluid may be evacuated from the fluid bag 10 by draining from the outlet 20 due to gravity. Accordingly, the fluid bag 10 may comprise means for hanging or otherwise attaching the fluid bag 10 to an IV pole or other apparatus used to facilitate administration of fluid from a fluid bag 10. In some embodiments, the means for hanging may comprise the slot 22, which may be used to hang the fluid bag 10 from a hook on an IV pole. However, other means for hanging include, for example, a clip or hook that may be integrated into or attached to the fluid bag 10 to facilitate hanging the fluid bag 10 from an IV pole or other apparatus. Another example means for evacuating fluid from the fluid bag 10 may comprise vacuuming fluid from the fluid bag 10 through the outlet 20, such as with an IV pump. The outlet 20 may accordingly provide a point of attachment for a tube or other means used to evacuate fluid from the fluid bag 10 and administer the fluid to a recipient, such as a patient for medicinal purposes.

In an exemplary embodiment of the present invention, the first side wall 12 carries one or more signaling tags 16. For purposes of discussion, only a single signaling tag 16 will be discussed, however, it will be appreciated that the side wall 12 may carry a plurality of signaling tags 16. In at least some embodiments, a signaling tag comprises a radio frequency (RF) tag. Accordingly, the description herein of some embodiments of the invention refers to a signaling tag (e.g., the signaling tag 16) as an RF tag for purposes of example to describe a radio frequency signal as one type of signal that may be emitted by a signaling tag. It will be appreciated, however, that a signaling tag, such as the signaling tag 16, may be configured to emit detectable signals other than radio frequency, such as, for example, ultrasound signals, optical signals, electrical current, electrical voltage, an electrical field, a magnetic field, and/or the like. In some embodiments, the signaling tag 16 comprises a sensor that may emit a signal dependent on a condition detected by the sensor. In some embodiments wherein the signaling tag 16 comprises a sensor, the signaling tag may comprise, for example, a Hall Effect sensor configured to output a voltage that varies in response to changes in a magnetic field to which the Hall Effect sensor is exposed.

In at least some embodiments, the second side wall 14 carries one or more inducers 18. For purposes of discussion, only a single inducer 18 will be discussed, however, it will be appreciated that the side wall 14 may carry a plurality of inducers 18. The inducer 18 may comprise any object or device that when positioned in sufficient proximity of a signaling tag 16 induces a change in state of a signal emitted by the signaling tag 16. In some embodiments, the inducer 18 comprises a second signaling tag, such as a signaling tag as described above in connection with the signaling tag 16. In this regard, the inducer 18 may comprise, for example, an RF tag. The inducer 18 of embodiments wherein the signaling tag 16 comprises a Hall Effect sensor may comprise a magnet or other magnetic field emitter.

In some embodiments, the signaling tag 16 and/or inducer 18 may be carried by the first side wall 12 and second side wall 14, respectively, such that the signaling tag 16 and/or inducer 18 are attached to or otherwise affixed to an inner or outer surface of the side walls 12 and 14. Alternatively, in some embodiments, the signaling tag 16 and/or inducer 18 may be integrated into the side walls 12 and 14 such that the signaling tags 16 and/or inducer 18 may be disposed within the side walls 12 and 14, respectively (e.g., between layers of the pliable material used to form the side walls 12 and 14). Still further, the exterior surfaces of the side walls 12 and 14 may include pockets for receiving and holding the RF tags, thereby permitting the signaling tag 16 and/or inducer 18 to be inserted prior to use of the fluid bag 10 and removed following use of the fluid bag such that the signaling tag 16 and/or inducer 18 may be reused, if so desired. Alternatively, the signaling tag 16 and/or inducer 18 may be carried by an adhesive strip that may be affixed to an outer surface of the side walls 12 and 14. In this regard, the adhesive strip may aid in the positioning of the signaling tag 16 and/or inducer 18.

The signaling tag 16 and inducer 18 are configured such that when the signaling tag 16 and inducer 18 come into sufficient proximity of each other (e.g., due to flexation of the side walls 12 and 14 as fluid is evacuated from the fluid bag 10), a change in the state of a signal emitted by the signaling tag 16 is triggered. Accordingly, the signaling tag 16 and inducer 18 are positioned in exemplary embodiments such that when fluid is evacuated from the fluid bag 10 and the sidewalls 12 and 14 flex inward due to evacuation of fluid from the fluid bag 10, the signaling tag 16 and inducer 18 are substantially parallel to each other and come within sufficient proximity to trigger a state change in a signal emitted by the signaling tag 16. When the volume of fluid in the fluid bag 10 is above a predefined threshold, the signaling tag 16 and inducer 18 are separated from each other due to the fluid in the bag, which causes the sidewalls 12 and 14 to flex outward, thus providing a buffer between the signaling tag 16 and inducer 18.

Figure 2:
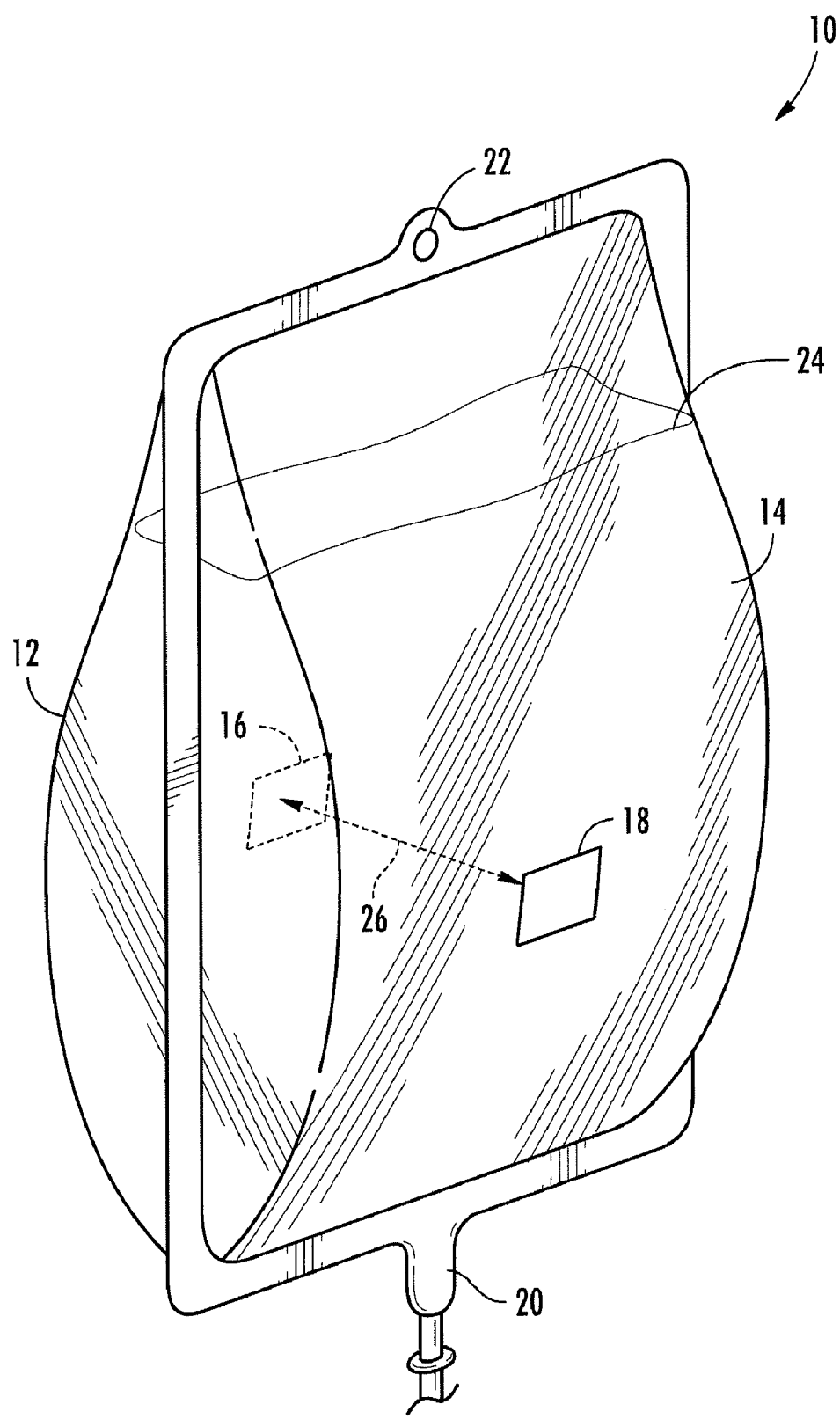
FIG. 2 illustrates a three-quarter perspective of a flexible fluid bag having a volume of fluid greater than a predefined threshold according to an exemplary embodiment of the present invention.

FIG. 2 illustrates a three-quarter perspective of a flexible fluid bag 10 having a volume of fluid greater than a predefined threshold according to an exemplary embodiment of the present invention. In this regard, FIG. 2 illustrates a fluid level 24 that is well above the level at which the signaling tag 16 and inducer 18 are carried by the side walls 12 and 14, respectively. The volume of fluid in the fluid bag 10 as illustrated in FIG. 2 is sufficient to cause the sidewalls 12 and 14 to flex outward, resulting in the spacing 26 between the signaling tag 16 and inducer 18. This spacing 26 is sufficiently large such that there is a buffer between the signaling tag 16 and inducer 18 and the state of a signal emitted by the signaling tag 16 is a known initial state defined to indicate that the volume of fluid in the fluid bag 10 is greater than a predefined threshold.

Figure 3:
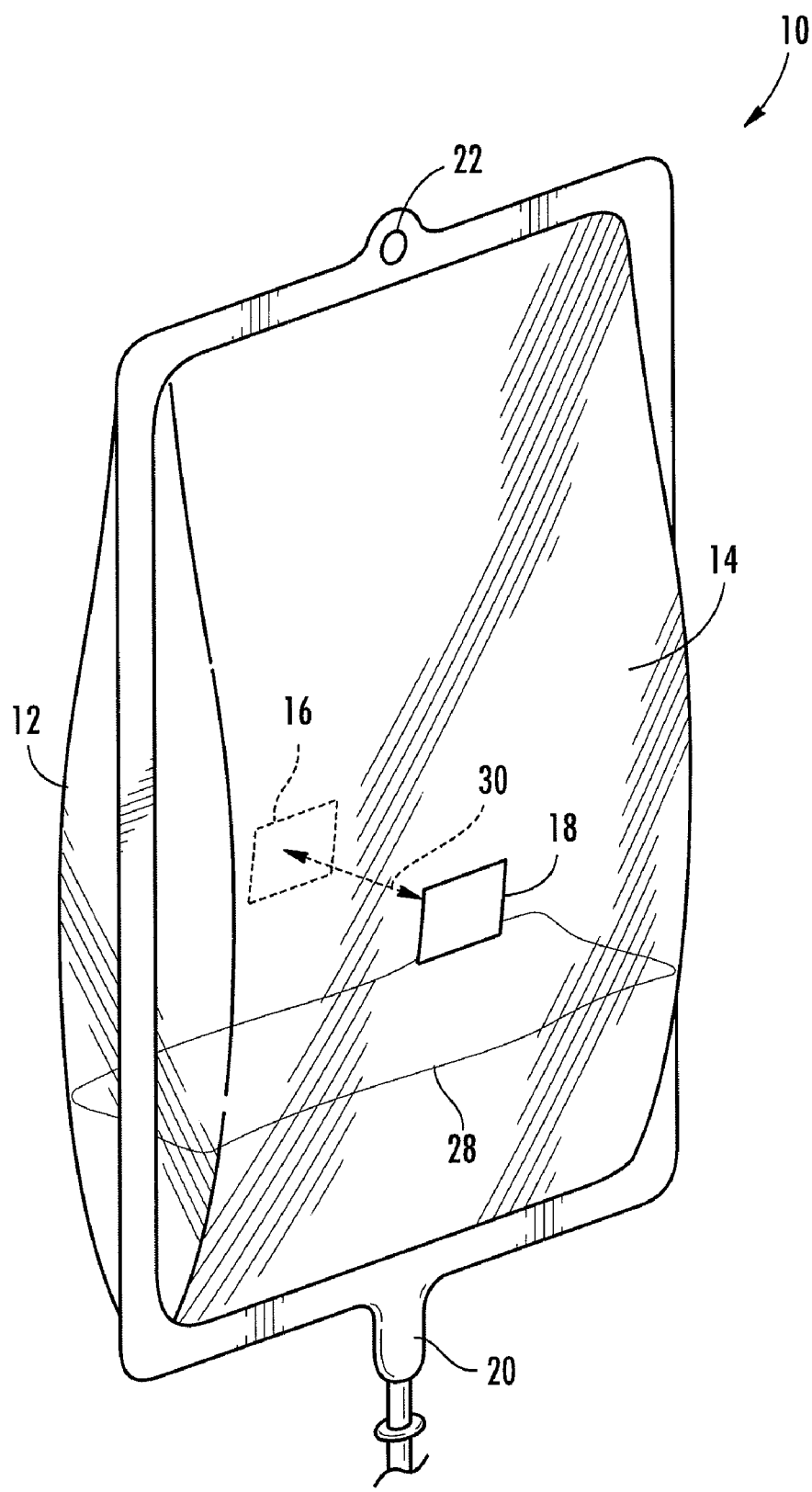
FIG. 3 illustrates a three-quarter perspective of a flexible fluid bag having a volume of fluid less than a predefined threshold according to an exemplary embodiment of the present invention.

As fluid is evacuated from the fluid bag 10 through the outlet 20, the volume of the fluid in the fluid bag 10 decreases and the sidewalls 12 and 14 flex inward. When the volume of fluid in the fluid bag 10 is less than the predefined threshold, the spacing between the signaling tag 16 and inducer 18 decreases such that the proximity between the signaling tag 16 and inducer 18 is sufficient to trigger a state change in a signal emitted by and the signaling tag 16. In this regard, FIG. 3 illustrates a three-quarter perspective of a flexible fluid bag 10 having a volume of fluid less than a predefined threshold according to an exemplary embodiment of the present invention. As illustrated in FIG. 3, the fluid level 28 is below the level at which the signaling tag 16 and inducer 18 are carried by the side walls 12 and 14, respectively. The side walls 12 and 14 have flexed inward toward each other and the spacing 30 between the signaling tag 16 and inducer 18 is significantly less than the spacing 26 illustrated in FIG. 2. The spacing 30 is sufficiently small such that the signaling tag 16 and inducer 18 are in sufficient proximity to trigger a change in the state of a signal emitted by the signaling tag 16, indicating that the volume of fluid in the fluid bag 10 is less than a predefined threshold. In one embodiment, the signaling tag 16 and inducer 18 being in "sufficient proximity" to trigger a change in state of a signal emitted by the signaling tag 16 comprises the signaling tag 16 and inducer 18 being within a predefined distance of each other.

The signaling tag 16 and inducer 18 may be vertically positioned on the side walls 12 and 14 such that a signal state change may be triggered at any predefined volume threshold. The volume threshold may be selected so as to give medical personnel sufficient time to take action to timely exchange a fluid bag 10 with a new fluid bag 10. Accordingly, the signaling tag 16 and inducer 18 may be positioned to enable alerting medical personnel of a low fluid volume in the bag.

It will be appreciated that the signal state change may comprise any change in state of the signaling tag 16 triggered by the signaling tag 16 and inducer 18 coming within sufficient proximity of each other due to flexation of the side walls 12 and 14. For example, in embodiments wherein both the signaling tag 16 and inducer 18 comprise RF tags, when the volume of fluid in the fluid bag 10 is greater than the predefined threshold, an antenna of the RF tags 16 may be detuned such that the antenna does not emit a readable or otherwise detectable signal. When the RF tags 16 and 18 come within sufficient proximity of each other, the RF tags 16 and 18 may couple, which may cause the detuned antenna to become tuned and emit a readable signal. Accordingly, in some embodiments, the signal state change comprises emission of a readable signal from the RF tag 16 when the RF tag 16 was not previously emitting a readable signal.

In another example, when the volume of fluid in the fluid bag 10 is greater than the predefined threshold, an antenna of the RF tag 16 may be configured to emit a readable or otherwise detectable signal. When the RF tags 16 and 18 come within sufficient proximity of each other, the RF tags 16 and 18 may couple, which may cause the antenna to become detuned and cease to emit a readable signal. Accordingly, in some embodiments, the signal state change comprises cessation of emission of a readable signal from the RF tag 16 when the RF tag 16 was previously emitting a readable signal.

In yet another example, the RF tags 16 and 18 may each comprise a primary antenna and a secondary antenna. The primary antenna may be configured to emit a readable or otherwise detectable signal when the volume of fluid in the fluid bag 10 is greater than the predefined threshold. The secondary antenna may be configured to be detuned such that the secondary antennas do not emit a readable signal when the volume of fluid in the fluid bag 10 is greater than the predefined threshold. When the RF tags 16 and 18 come within sufficient proximity of each other, the secondary antennas may be activated and emit a readable signal. Accordingly, in some embodiments, the signal state change comprises emission of a second or new readable signal from the RF tag 16. The new emitted signal may be in addition to that initially emitted by the primary antennas or in lieu of the initial signal emitted when the volume of fluid was greater than the predefined threshold.

In a further example, the RF tag 16 may be configured to emit a signal having a first communication field and/or a first frequency when the volume of fluid in the fluid bag 10 is greater than the predefined threshold. When the RF tags 16 and 18 come within sufficient proximity of each other as fluid is evacuated from the fluid bag 10 such that the volume of fluid is less than the predefined threshold, the RF tag 16 may be configured to emit a signal having a second communication field and/or a second frequency. A reader or interrogator used to monitor a state of a signal emitted by the RF tag 16 may be configured to differentiate between the first and second communication fields. In some embodiments, the first communication field may comprise a near-field UHF signal that has different characteristics and properties from the second communication field, which may comprise a far-field UHF signal. There could be two individual readers and/or two antennas connected to a reader, one with near field capabilities and one with far field capabilities such that when one of the readers picks up the change in state of the communication field this triggers the message for replenishment. In another scenario the same reader could have the capability of reading both near field and far field signals such that the change in state within the single reader triggers the message for replenishment. Accordingly, a reader and/or an antenna connected to a reader may be positioned at a sufficient distance from an emitting RF tag such that only the signal having the second frequency is detectable such that the low fluid volume condition may be detected. In other embodiments, the second frequency may comprise a far-field UHF signal that is readable only from a relatively close proximity to the RF tag emitting a signal having the first frequency. The first frequency may comprise a far-field UHF signal that is readable from a farther distance away from the RF tag than the second frequency. Accordingly, a reader and/or an antenna connected to a reader may be positioned a sufficient distance such that only the signal having the first frequency is detectable such that the low fluid volume condition may be detected when the reader no longer detects a signal emitted from the RF tag 16 and/or RF tag 18.

In another example, the signaling tag 16 may vary the amplitude (e.g., increasing the amplitude, decreasing the amplitude, or the like) of an emitted signal such that a reader may detect the amplitude variation when the signaling tag 16 and inducer 18 come within sufficient proximity of each other, thus indicating that the volume of fluid in the fluid bag 10 is below the predefined threshold.

In embodiments wherein the signaling tag 16 comprises a Hall Effect sensor and the inducer 18 comprises a magnet or other magnetic field emitter, the signal state change may comprise a change in a voltage level emitted or otherwise output by the Hall Effect sensor. In this regard, when the signaling tag 16 comes within sufficient proximity of a magnetic field emitted by the inducer 18, the state of an output voltage emitted by the Hall Effect sensor may be induced to change.

It will be appreciated that the above described example changes in signal state are merely examples of some embodiments of the invention. Accordingly, embodiments of the invention may utilize any measurable change in signal state triggered when the signaling tag 16 and inducer 18 come within sufficient proximity of each other.

It will be further appreciated that the signaling tag 16 may comprise either an active tag or a passive tag (e.g., an active or passive RF tag). Accordingly, a reader used to monitor a state of a signal emitted by the signaling tag 16 may be configured to passively monitor the signal state or to actively interrogate the signaling tag 16. Accordingly, any signal emitted by the signaling tag 16 may be emitted in response to being interrogated by a reader, if the signaling tag 16 is embodied as a passive tag.

Figure 4:
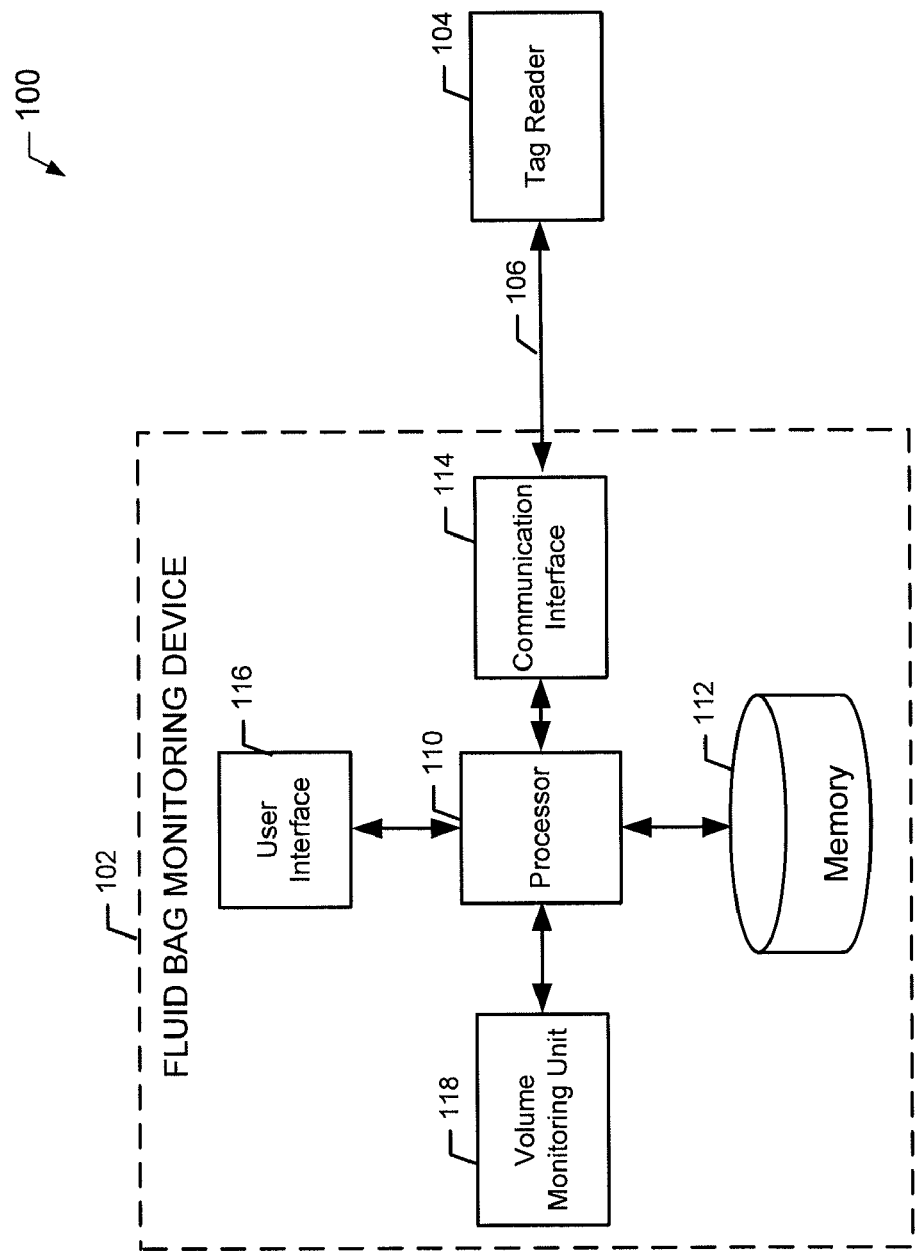
FIG. 4 illustrates a block diagram of a system for monitoring a volume of fluid in a flexible fluid bag according to an exemplary embodiment of the present invention.

Embodiments of the invention further provide systems and devices for monitoring a volume of fluid in a fluid bag 10 through detection of a state of a signal emitted by the signaling tag 16. In this regard, FIG. 4 illustrates a block diagram of a system 100 for monitoring a volume of fluid in a flexible fluid bag 10 according to an exemplary embodiment of the present invention. The system 100 comprises a fluid bag monitoring device 102 and a tag reader 104 in communication over the communications link 106. The fluid bag monitoring device 102 may be embodied as or on any computing device or plurality of computing devices. In some embodiments, the fluid bag monitoring device 102 may be embodied on an IV pump. In other embodiments, the fluid bag monitoring device 102 may be embodied as a computing device located at a nurse's station.

The tag reader 104 may be embodied as any signaling tag reader configured to read a signal emitted by the signaling tag 16 such that a change in state of the signal may be detected. In this regard, the tag reader 104 may be embodied, for example, as an RF tag reader. Depending on embodiments of the signaling tag 16, the tag reader 104 may passively read an emitted signal (e.g., for an active RF tag) or to actively interrogate the signaling tag 16 (e.g., for a passive RF tag). The tag reader 104 may be located anywhere within sufficient proximity to detect a change in state of a signal emitted by the signaling tag 16. The tag reader 104 may be configured to read and/or monitor a voltage output by the signaling tag 16, such as in embodiments wherein the signaling tag 16 comprises a Hall Effect sensor. The tag reader 104 may be mounted, for example, on an IV pole from which the fluid bag 10 is hung, embedded into an IV pump, mounted to the IV pump, or on the fluid bag 10. Although referred to as a tag reader, it will be appreciated that the tag reader 104 may comprise a system comprising a plurality of components. For example, the tag reader 104 may comprise a tag reader component connected to one or more antennas configured to receive a signal emitted by a signaling tag 16 and transmit the signal to the tag reader component so that the tag reader component may read the signal.

In some embodiments, the communications link 106 comprises a direct wired connection or wireless communications link between the tag reader 104 and fluid bag monitoring device 102. In other embodiments, the communications link 106 comprises a network (e.g., a wireline network, wireless network, or some combination thereof) through which the tag reader 104 and fluid bag monitoring device 102 are interfaced.

Referring now to the fluid bag monitoring device 102, in an exemplary embodiment, the fluid bag monitoring device 102 includes various means, such as a processor 110, memory 112, communication interface 114, user interface 116, and volume monitoring unit 118 for performing the various functions herein described. These means of the fluid bag monitoring device 102 as described herein may be embodied as, for example, hardware elements (e.g., a suitably programmed processor, combinational logic circuit, and/or the like), a computer program product comprising computer-readable program instructions (e.g., software or firmware) stored on a computer-readable medium (e.g. memory 122) that is executable by a suitably configured processing device (e.g., the processor 120), or some combination thereof. The processor 110 may, for example, be embodied as various means including a microprocessor, a coprocessor, a controller, or various other processing elements including integrated circuits such as, for example, an ASIC (application specific integrated circuit) or FPGA (field programmable gate array). In an exemplary embodiment, the processor 110 is configured to execute instructions stored in the memory 112 or otherwise accessible to the processor 110. These instructions, when executed by the processor 110, may cause the fluid bag monitoring device 102 to perform one or more of the functionalities of the fluid bag monitoring device 102 as described herein. Although illustrated in FIG. 4 as a single processor, in some embodiments the processor 110 comprises a plurality of processors.

The memory 112 may include, for example, volatile and/or non-volatile memory. Although illustrated in FIG. 4 as a single memory, the memory 112 may comprise a plurality of memories. The memory 112 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. The memory 112 may be configured to store information, data, applications, instructions, or the like for enabling the fluid bag monitoring device 102 to carry out various functions in accordance with exemplary embodiments of the present invention. For example, in at least some embodiments, the memory 112 is configured to buffer input data for processing by the processor 110. Additionally or alternatively, in at least some embodiments, the memory 112 is configured to store program instructions for execution by the processor 110. The memory 112 may comprise one or more databases that store information in the form of static and/or dynamic information. This stored information may be stored and/or used by the volume monitoring unit 118 during the course of performing its functionalities.

The communication interface 114 may be embodied as any device or means embodied in hardware, a computer program product comprising computer readable program instructions stored on a computer readable medium (e.g., the memory 112) and executed by a processing device (e.g., the processor 110), or any combination thereof that is configured to receive and/or transmit data from/to a remote device, such as a tag reader 104 over the communications link 106. In at least one embodiment, the communication interface 114 is at least partially embodied as or otherwise controlled by the processor 110. The communication interface 114 may include, for example, an antenna, a transmitter, a receiver, a transceiver and/or supporting hardware or software for enabling communications with the tag reader 104. The communication interface 114 may be configured to receive and/or transmit data using any protocol that may be used for communications with the tag reader 104 over the communications link 106. In an exemplary embodiment, the communication interface 114 is configured to receive an indication of a detected state of a signal emitted by the RF tag 16 and/or RF tag 18 from the tag reader 104. The communication interface 114 may additionally be in communication with the memory 112, user interface 116, and/or volume monitoring unit 118, such as via a bus.

The user interface 116 may be in communication with the processor 110 to receive an indication of a user input and/or to provide an audible, visual, mechanical, or other output to the user. As such, the user interface 116 may include, for example, a keyboard, a mouse, a joystick, a display, a touch screen display, a microphone, a speaker, and/or other input/output mechanisms. The user interface 116 may accordingly provide means to provide notice to a user when the volume of fluid in a fluid bag 10 is detected to be below a predefined threshold. The user interface 116 may be in communication with the memory 112, communication interface 114, and/or volume monitoring unit 118, such as via a bus.

The volume monitoring unit 118 may be embodied as various means, such as hardware, a computer program product comprising computer readable program instructions stored on a computer readable medium (e.g., the memory 112) and executed by a processing device (e.g., the processor 110), or some combination thereof, and, in one embodiment, is embodied as or otherwise controlled by the processor 110. In embodiments where the volume monitoring unit 118 is embodied separately from the processor 110, the volume monitoring unit 118 may be in communication with the processor 110. The volume monitoring unit 118 is configured to monitor the state of signal emitted by the signaling tag 16 as read and supplied by the tag reader 104. The volume monitoring unit 118 is further configured to detect a change in state of the signal, which is indicative of the volume of fluid in the fluid bag 10 being below a predefined threshold due to evacuation of fluid from the bag.

When the volume monitoring unit 118 detects a change in state of a signal emitted by the signaling tag 16 and thus a low volume condition, the volume monitoring unit 118 may be further configured to provide notice that the volume of fluid in a fluid bag 10 has been detected to be below the predefined threshold. This notice may comprise, for example, triggering an audible alert that may be annunciated through the user interface 116. Additionally or alternatively, the notice may comprise a graphical notice that may be displayed on a display associated with the user interface 116. In some embodiments, the notice may comprise sending a notification to a user device of medical personnel responsible for changing out an IV bag. In this regard, the volume monitoring unit 118 may, for example, be configured to send an email, instant message, text message, and/or the like to a mobile phone, pager, or other mobile device carried by medical personnel. Accordingly, responsible medical personnel may be alerted to a low fluid volume condition and may take appropriate action, such as replacing the fluid bag 10.

In some embodiments, a signal emitted by the signaling tag 16 may carry a unique code or other signaling tag identifier that identifies the particular signaling tag 16. This signaling tag identifier may be read by the tag reader 104 and may be interpreted by the volume monitoring unit 118. The signaling tag identifier may further be associated with a particular IV bag, medication, physician identification, patient identification, patient room number, and/or the like. In this regard, the volume monitoring unit 118 may be configured to store information, such as in a database, in the memory 112 related to signaling tag identifiers for one or more signaling tags 16. The signaling tag identifiers may be stored in association with additional information, such as an IV bag identifier, medication name, physician identification, patient identification, patient room number, and/or the like. In some embodiments, the volume monitoring unit 118 may be configured to retrieve information associated with a particular signaling tag 16 by determining the signaling tag identifier from a detected signal read by the tag reader 104 and looking up the signaling tag identifier in the memory 112 to retrieve the information associated with the signaling tag 16. The volume monitoring unit 118 may further be configured to provide the associated information to a user over the user interface 116.

The volume monitoring unit 118 may be configured to generate an association between a signaling tag identifier carried by a signal emitted by the signaling tag 16 and other information. In this regard, the volume monitoring unit 118 may be configured to determine a signaling tag identifier carried by a signal emitted by a signaling tag 16 and read by the tag reader 104 and generate an entry in a database for the signaling tag identifier. The volume monitoring unit 118 may be configured to further prompt a user over the user interface 114 to enter information to store in association with the signaling tag identifier. Additionally or alternatively, the volume monitoring unit 118 may be configured to automatically determine information to store in association with the signaling tag identifier. For example, the tag reader 104 may be configured to determine an identity of a patient and/or fluid bag 10 by optically scanning a bar code that may be printed on a patient's arm band and/or a bar code that may be printed on the fluid bag 10.

Figure 5:
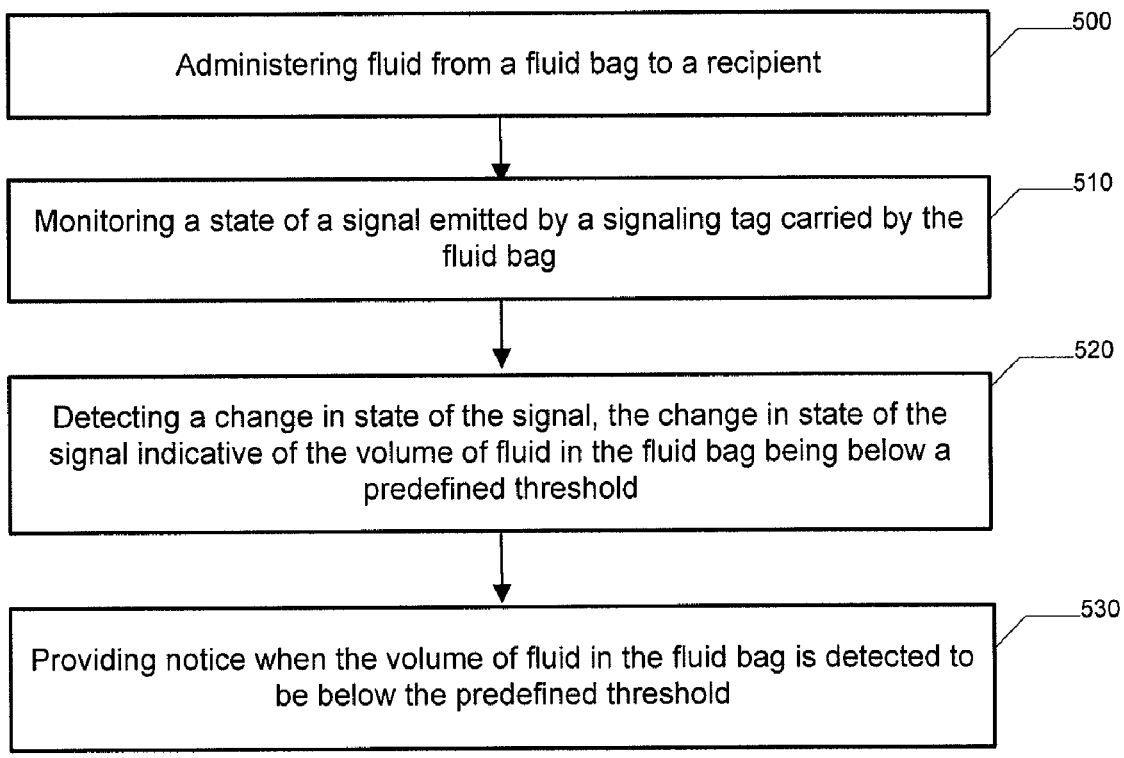
FIG. 5 is a flowchart according to an exemplary method for monitoring a volume of fluid in a flexible fluid bag according to an exemplary embodiment of the present invention.

FIG. 5 is a flowchart of a system, method, and computer program product according to exemplary embodiments of the invention. It will be understood that each block or step of the flowcharts, and combinations of blocks in the flowcharts, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may be stored by one or more memory devices of a mobile terminal, server, or other computing device and executed by a processor in the computing device. In some embodiments, the computer program instructions comprising the computer program product(s) which embody the procedures described above may be stored by memory devices of a plurality of computing devices. As will be appreciated, any such computer program product may be loaded onto a computer or other programmable apparatus to produce a machine, such that the instructions of the computer program product which execute on the computer or other programmable apparatus create means for implementing the functions specified in the flowchart block(s) or step(s). Further, the computer program product may comprise one or more computer-readable memories on which the computer program instructions may be stored such that the one or more computer-readable memories can direct a computer or other programmable apparatus to function in a particular manner, such that the computer program product comprises an article of manufacture including instruction means which implement the function specified in the flowchart block(s) or step(s). The computer program instructions of one or more computer program products may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions specified in the flowchart block(s) or step(s).

Accordingly, blocks or steps of the flowchart support combinations of means for performing the specified functions, combinations of steps for performing the specified functions and program instruction means for performing the specified functions. It will also be understood that one or more blocks or steps of the flowchart, and combinations of blocks or steps in the flowchart, may be implemented by special purpose hardware-based computer systems which perform the specified functions or steps, or combinations of special purpose hardware and computer instructions.

In this regard, one exemplary method for monitoring a volume of fluid in a flexible fluid bag 10 according to an exemplary embodiment of the present invention is illustrated in FIG. 5. The method includes administering fluid from the fluid bag 10 to a recipient, at operation 500. Operation 510 comprises the tag reader 104 and/or volume monitoring unit 118 monitoring the state of a signal emitted by the signaling tag 16. The method further includes the volume monitoring unit 118 detecting a change in state of the signal, which is indicative of the volume of fluid in the fluid bag 10 being below a predefined threshold, at operation 520. Operation 530 comprises the volume monitoring unit 118 providing notice that the volume of fluid in the fluid bag 10 is below the predefined threshold.

The above described functions may be carried out in many ways. For example, any suitable means for carrying out each of the functions described above may be employed to carry out embodiments of the invention. In one embodiment, a suitably configured processor may provide all or a portion of the elements of the invention. In another embodiment, all or a portion of the elements of the invention may be configured by and operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

As such, then, embodiments of the invention provide a flexible fluid bag, such as may be used for administration of intravenous fluids, which facilitates detection when a volume of fluid remaining in the fluid bag is less than a predefined threshold. Embodiments of the invention further provide a method and computer program product for monitoring a volume of fluid in such flexible fluid bags to detect when the volume of fluid therein is less than the predefined threshold. Accordingly, embodiments of the invention enable detection of a low fluid volume level within a fluid bag and notification of the low fluid volume status when such a condition is detected.

Many modifications and other embodiments of the inventions set forth herein will come to mind to one skilled in the art to which these inventions pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A flexible fluid bag formed of pliable material, the fluid bag comprising:
    a first side wall;
    a second side wall opposing the first side wall;
    an outlet through which fluid contained in the fluid bag is evacuated;
    a signaling tag carried by the first side wall; and
    an inducer carried by the second side wall;
    wherein the signaling tag and inducer are positioned such that when a volume of fluid in the fluid bag is less than a predefined threshold, the signaling tag and inducer come into a sufficient proximity due to flexation of at least a portion of one or more of the first or second sidewalls of the fluid bag as fluid is evacuated from the fluid bag to trigger a state of a signal emitted by the signaling tag to change.

2. A flexible fluid bag according to claim 1, wherein:
the signaling tag comprises a first radio frequency tag; and
the inducer comprises a second radio frequency tag.

3. A flexible fluid bag according to claim 1, wherein:
the signaling tag comprises a passive radio frequency tag comprising an antenna, and the inducer comprises a second radio frequency tag, wherein the antenna is configured to become detuned when the signaling tag is coupled to the inducer due to being in a sufficient proximity of the inducer; and
the signal state change triggered when the signaling tag and inducer come into a sufficient proximity comprises cessation of emission of a readable signal from the signaling tag due to coupling of the signaling tag and the inducer.

4. A flexible fluid bag according to claim 1, wherein:
the signaling tag comprises a primary antenna configured to emit a readable signal and a secondary antenna configured to be detuned when the volume of fluid in the fluid bag is greater than the predefined threshold, wherein the secondary antenna is further configured to be activated such that the secondary antenna emits a readable signal when the first signaling tag comes within a sufficient proximity of the inducer when the volume of fluid in the fluid bag is less than the predefined threshold; and
the signal state change triggered when the signaling tag and inducer come into a sufficient proximity comprises emission of a readable signal from the secondary antenna of the signaling tag.

5. A flexible fluid bag according to claim 1, wherein:
the signaling tag is configured to emit a first signal when the volume of fluid in the fluid bag is greater than the predefined threshold and to emit a second signal when the signaling tag comes within a sufficient proximity of the inducer when the volume of fluid in the fluid bag is less than the predefined threshold; and
the signal state change triggered when the signaling tag and inducer come into a sufficient proximity comprises emission of the second signal from the signaling tag.

6. A flexible fluid bag according to claim 1, wherein:
the signaling tag comprises a Hall Effect sensor;
the inducer comprises a magnetic field emitter; and
the signal state change triggered when the signaling tag and inducer come into a sufficient proximity comprises a change in a voltage emitted by the signaling tag.

7. A flexible fluid bag according to claim 1, wherein the flexible fluid bag comprises an intravenous bag and wherein the fluid in the intravenous bag comprises a medication for intravenous administration.

8. A method for monitoring a volume of fluid in a flexible fluid bag, the method comprising:
administering the fluid from the fluid bag to a recipient, wherein the fluid bag comprises a first side wall, a second side wall opposing the first side wall, an outlet through which fluid contained in the fluid bag is evacuated for administration to a recipient, a signaling tag carried by the first side wall, and an inducer carried by the second side wall; and
detecting a change in state of a signal emitted by the signaling tag as a result of the signaling tag and inducer coming into a sufficient proximity of one another due to flexation of at least a portion of one or more of the first or second sidewalls of the fluid bag as fluid is evacuated therefrom, wherein the change in state of the signal is indicative of the volume of fluid in the fluid bag being below a predefined threshold.

9. A method according to claim 8, further comprising providing notice when the volume of fluid is detected to be below the predefined threshold.

10. A method according to claim 8, wherein the signaling tag and inducer comprise radio frequency tags.

11. A method according to claim 8, wherein the signaling tag comprises a Hall Effect sensor and wherein the inducer comprises a magnetic field emitter; and wherein detecting a change in state of a signal emitted by the signaling tag comprises detecting a change in an output voltage emitted by the signaling tag.

12. A method according to claim 8, wherein the flexible fluid bag comprises an intravenous bag and the fluid in the intravenous bag comprises a medication for intravenous administration; and wherein:
administering the fluid from the fluid bag to a recipient comprises administering the medication to a patient.

13. A method according to claim 8, wherein detecting a change in state of a signal emitted by the signaling tag comprises detecting a cessation of emission of a readable signal from the signaling tag.

14. A method according to claim 8, wherein detecting a change in state of a signal emitted by the signaling tag comprises detecting emission of a second signal from the signaling tag.

15. A method according to claim 8, wherein detecting a change in state of a signal emitted by the signaling tag comprises detecting emission of a signal from the signaling tag having a different communication field than a signal previously emitted from the signaling tag.

16. A computer program product for monitoring a volume of fluid in a flexible fluid bag, the fluid bag comprising a first side wall, a second side wall opposing the first side wall, an outlet through which fluid contained in the fluid bag is evacuated for administration to a recipient, a signaling tag carried by the first side wall, and an inducer carried by the second side wall; wherein the computer program product comprises at least one computer-readable storage medium having computer-readable program instructions stored therein, the computer-readable program instructions comprising:
a program instruction for monitoring a state of a signal emitted by the signaling tag while fluid from the fluid bag is administered to a recipient; and
a program instruction for detecting a change in state of a signal emitted by the signaling tag as a result of the signaling tag and inducer coming into a sufficient proximity of one another due to flexation of at least a portion of one or more of the first or second sidewalls of the fluid bag as fluid is evacuated therefrom, wherein the change in state of the signal is indicative of the volume of fluid in the fluid bag being below a predefined threshold.

17. A computer program product according to claim 16, further comprising:
a program instruction for providing notice when the volume of fluid is detected to be below the predefined threshold.

18. A computer program product according to claim 16, wherein the flexible fluid bag comprises an intravenous bag and the fluid in the intravenous bag comprises a medication for intravenous administration.

19. A computer program product according to claim 16, wherein the program instruction for detecting a change in state of a signal emitted by the signaling tag comprises instructions for detecting a cessation of emission of a readable signal from the signaling tag.

20. A computer program product according to claim 16, wherein the program instruction for detecting a change in state of a signal emitted by the signaling tag comprises instructions for detecting emission of a second signal from the signaling tag.

21. A computer program product according to claim 16, wherein the program instruction for detecting a change in state of a signal emitted by the signaling tag comprises instructions for detecting emission of a signal from the signaling tag having a different communication field than a signal previously emitted from the signaling tag.

22. A computer program product according to claim 16, wherein the program instruction for detecting a change in state of a signal emitted by the signaling tag comprises instructions for detecting a change in an output voltage emitted by the signaling tag.

* * * * *